(12) United States Patent
Coleman

(10) Patent No.: US 11,259,952 B1
(45) Date of Patent: Mar. 1, 2022

(54) SYSTEM AND METHOD FOR SIZING DEVICE AND ERECTION RING

(71) Applicant: Joshua M. Coleman, Moapa, NV (US)

(72) Inventor: Joshua M. Coleman, Moapa, NV (US)

( * ) Notice: Subject to any disclaimer, the term of this patent is extended or adjusted under 35 U.S.C. 154(b) by 0 days.

(21) Appl. No.: 17/349,187

(22) Filed: Jun. 16, 2021

(51) Int. Cl.
*A61F 5/41* (2006.01)
*A61B 5/107* (2006.01)

(52) U.S. Cl.
CPC .............. *A61F 5/41* (2013.01); *A61B 5/1072* (2013.01); *A61B 5/1075* (2013.01); *A61B 2560/04* (2013.01); *A61F 2005/411* (2013.01); *A61F 2005/414* (2013.01)

(58) Field of Classification Search
CPC .......... A61F 5/41; A61B 5/107; A61B 5/1072
See application file for complete search history.

(56) References Cited

U.S. PATENT DOCUMENTS

| | | | |
|---|---|---|---|
| 4,203,432 A | 5/1980 | Koch | |
| 4,428,385 A | 1/1984 | Morales | |
| 4,875,296 A * | 10/1989 | Holzmeister | G01B 3/004 33/770 |
| 4,960,131 A | 10/1990 | Koss | |
| 5,779,621 A | 7/1998 | Chaney | |
| 5,810,710 A | 9/1998 | Burgos | |
| 6,659,938 B1 | 12/2003 | Orlowski et al. | |
| 9,308,117 B2 | 4/2016 | Oh et al. | |
| D803,078 S * | 11/2017 | Chan | D10/71 |
| 2004/0129277 A1* | 7/2004 | Parkes | A61F 2/0054 128/885 |
| 2016/0058603 A1* | 3/2016 | Vanderwolk | A61F 5/41 600/38 |
| 2019/0254862 A1* | 8/2019 | Tucker | A61F 5/41 |

* cited by examiner

*Primary Examiner* — John P Lacyk
(74) *Attorney, Agent, or Firm* — Christopher Mayle; Bold IP, PLLC

(57) ABSTRACT

A system and method directed for a sizing device and erectile ring is described where the sizing device properly measures one's girth to correctly find the proper size erection ring. The sizing device has a measuring tape that will slide through a plurality of perimeter components with a track running through each of the perimeter components for the measuring tape to easily travel through whereby a measurement is then obtained when the perimeter components come into contact with the penis whereby then an erectile is created from the sizing.

20 Claims, 5 Drawing Sheets

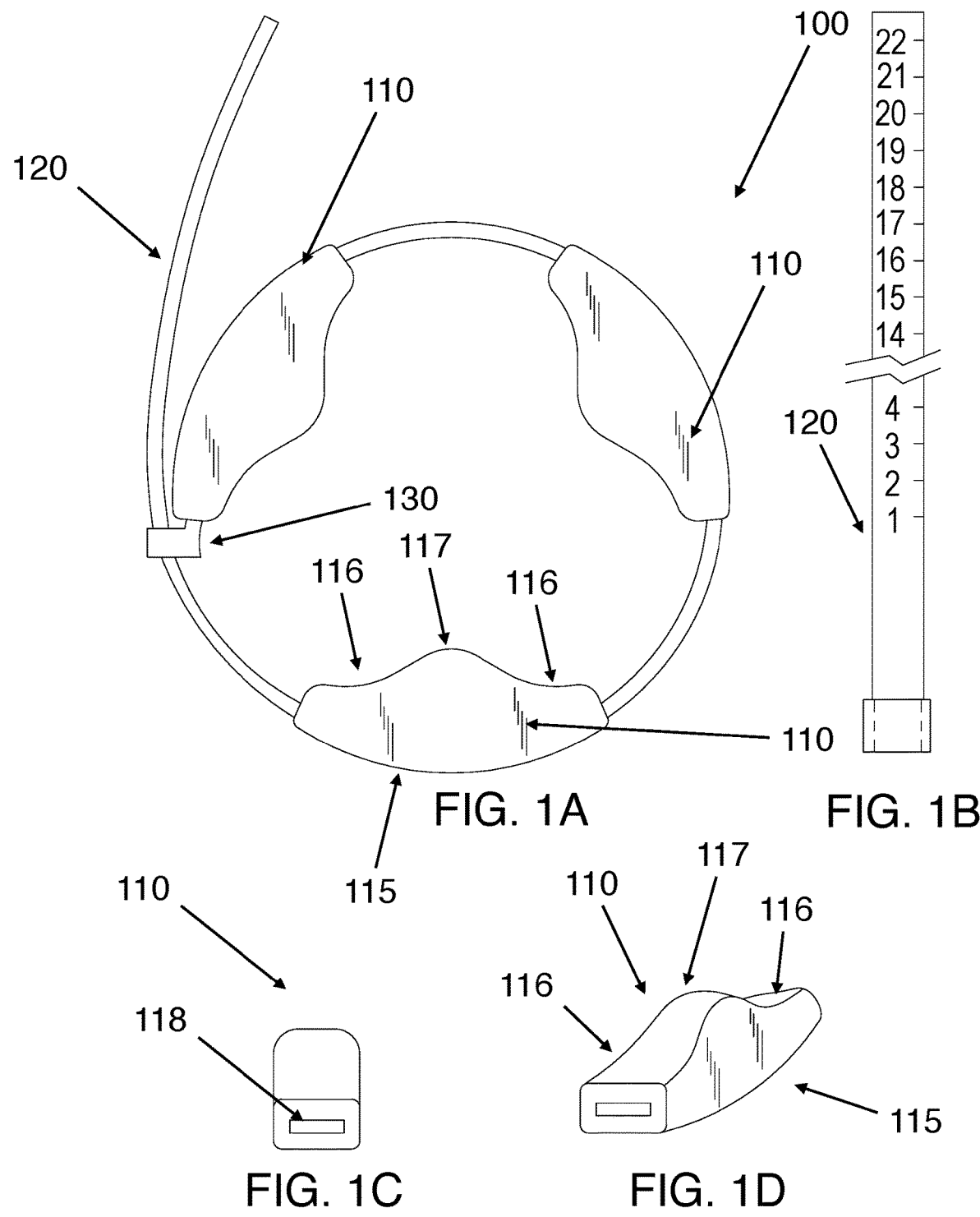

SYSTEM AND METHOD FOR SIZING DEVICE AND ERECTION RING

FIELD OF DISCLOSURE

The field of disclosure is generally directed to a sizing device and a ring for enhancing male functions, and more particularly to a sizing device made of multiple segments that may be decreased or increased in size to provide proper measurement of a penis.

BACKGROUND

One of the causes of erectile dysfunction can be that the body can't keep enough blood in the penis to get an erection started or keep an erection going. A penis ring will trap blood in the penis for longer and increases the total amount of blood in the penis for a stronger erection. Typical penis rings do not have an ergonomic shape suited for the biology of the penis and are improperly sized, leading to reduction in blood flow and diminishing the effectiveness of the ring. Thus, a new and improved sizing device and ring is needed to remedy the aforementioned problems.

SUMMARY

The disclosure presented herein relates to a sizing device for a penis, the sizing device including: a plurality of components and a measurement strip, the plurality of components having an aperture for providing access to a length of measurement strip to pass through, a holder connected to one of the plurality of components whereby one end of the measurement strip is connected to the holder, whereby a second end of the measurement strip passes through the holder, the holder having a latch mechanism for gripping the measurement strip, the plurality of components each having a rectangular arching outer portion and a bulbous inner portion configured to come into contact with an outer perimeter of the penis, the plurality of components having an outer convex surface on one end and two inner concave surfaces on an opposite end, the inner concave surfaces extending into an inner convex surface positioned between the inner concave surfaces, the inner convex surface having a curve facing an opposite direction from a curve in outer convex surface, whereby a length of the outer convex surface is equal to the length of the inner concave surfaces and the inner convex surface, whereby the inner convex surface and the inner concave surfaces have deeper bends than the outer convex surface.

The disclosure presented herein also relates to a sizing system for a penis including: a sizing device and an erectile ring, the sizing device having a plurality of components and a measurement strip, the plurality of components having an aperture for providing access to a length of measurement strip to pass through, whereby the sizing device has a holder connected to one of the plurality of components whereby one end of the measurement strip is connected to the holder, whereby a second end of the measurement strip passes through the holder, whereby the holder having a latch mechanism for gripping the measurement strip, the plurality of components each having a rectangular arching outer portion and a bulbous inner portion configured to come into contact with an outer perimeter of the penis, the plurality of components having an outer convex surface on one end and two inner concave surfaces on an opposite end, the inner concave surfaces extending into an inner convex surface positioned between the inner concave surfaces, the inner convex surface having a curve facing an opposite direction from a curve in the outer convex surface, a length of the outer convex surface is equal to the length of the inner concave surfaces and the inner convex surface, the inner convex surface and the inner concave surfaces have deeper bends than the outer convex surface, whereby the erectile ring is circular and has a three inner three prong aperture, whereby the erectile ring has an aperture with three concave surfaces with a curve extending outward to an outer perimeter, whereby between each concave surface there is convex surface facing inward to a center of the aperture, whereby the erectile ring has an aperture with an arching concave surface with a curve extending outward to an outer perimeter, whereby each arching concave surface is connected to two convex surfaces inward to a center of the aperture, the convex surfaces extending into a second concave surface positioned between the convex surfaces.

The disclosure presented herein also relates to a method for a sizing device for a penis, the method including: measuring a penis with a sizing device including: a plurality of components and a measurement strip, the plurality of components having an aperture for providing access to a length of measurement strip to pass through, the sizing device comprising a holder connected to one of the plurality of components whereby one end of the measurement strip is connected to the holder, whereby a second end of the measurement strip passes through the holder, creating an erectile ring in response to the measurement, the erectile ring having an aperture with three concave surfaces with a curve extending outward to an outer perimeter, whereby between each concave surface there is convex surface facing inward to a center of the aperture, and creating an erectile ring in response to the measurement, the erectile ring has an aperture with an arching concave surface with a curve extending outward to an outer perimeter, whereby the arching concave surface is connected to two convex surfaces inward to a center of the aperture, the convex surfaces extending into a second concave surface positioned between the convex surfaces.

BRIEF DESCRIPTION OF DRAWINGS

The present invention will be described by way of exemplary embodiments, but not limitations, illustrated in the accompanying drawings in which like references denote similar elements, and in which:

FIG. 1A-1D illustrate an embodiment of a sizing device in accordance with the present invention.

DETAILED DESCRIPTION

Figure 2A:
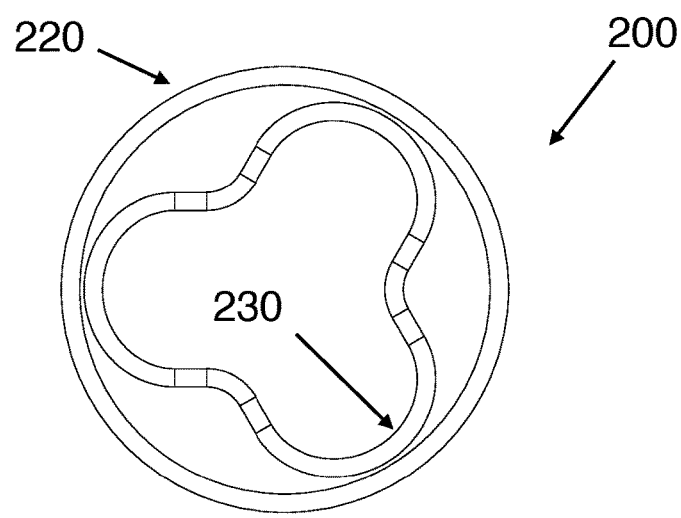
FIG. 2A-2C illustrate an embodiment of an erectile ring.
Figure 2B:
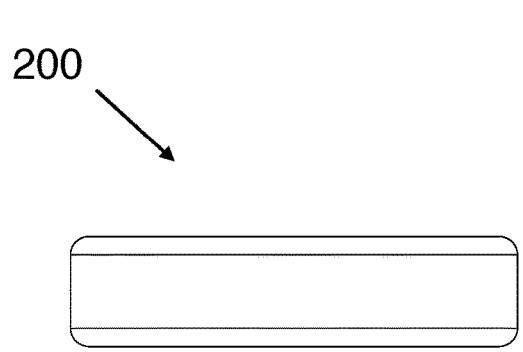
Figure 2C:
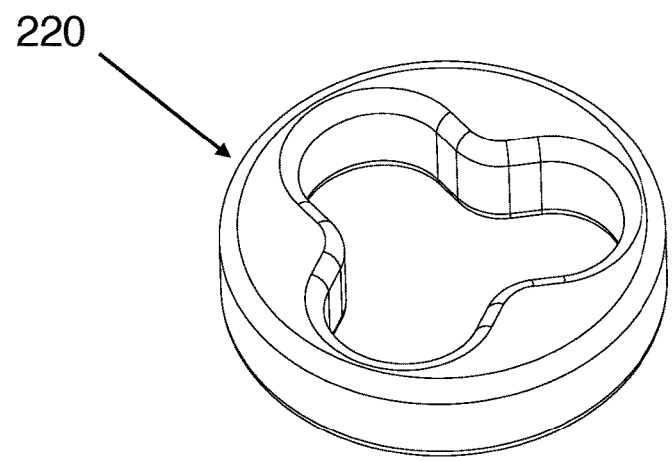
Figure 3A:
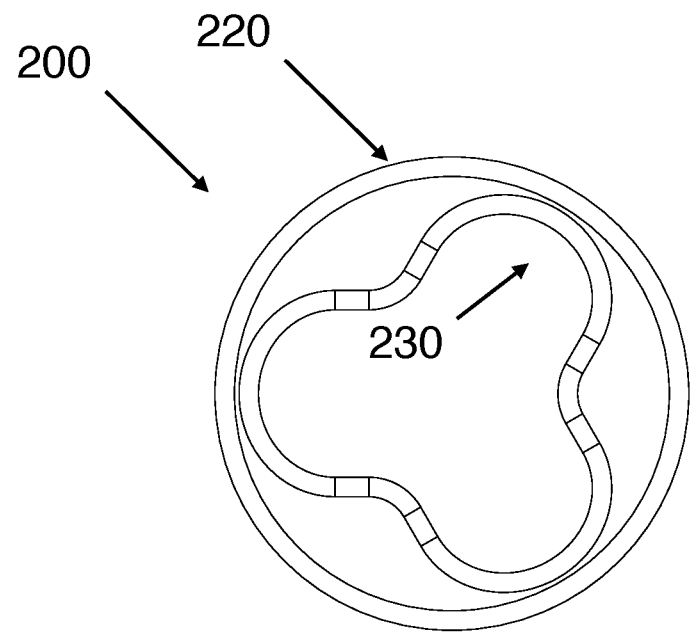
FIG. 3A-3B illustrate other views of the erectile ring of FIG. 2.
Figure 3B:
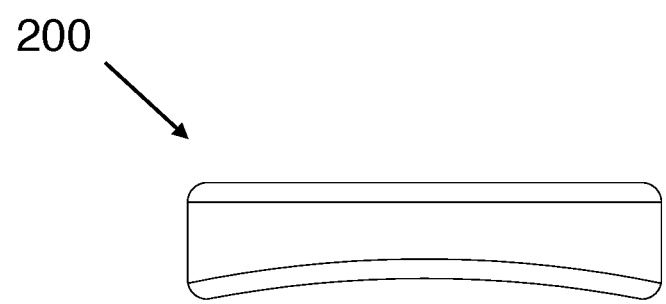
Figure 4A:
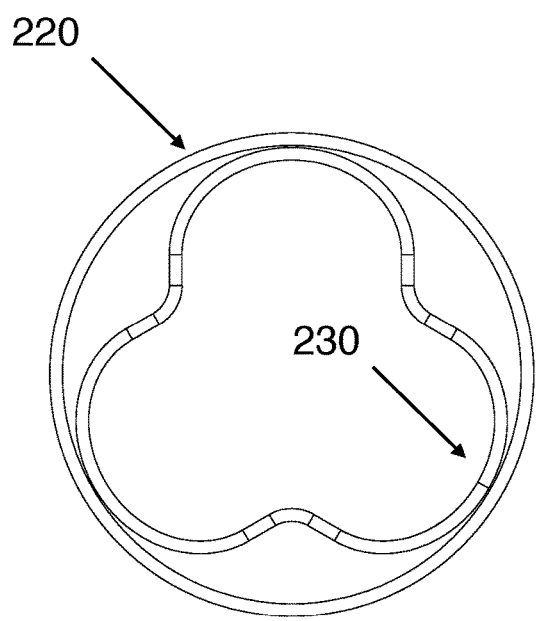
FIG. 4A-4C illustrate other views of the erectile ring of FIG. 2.
Figure 4B:
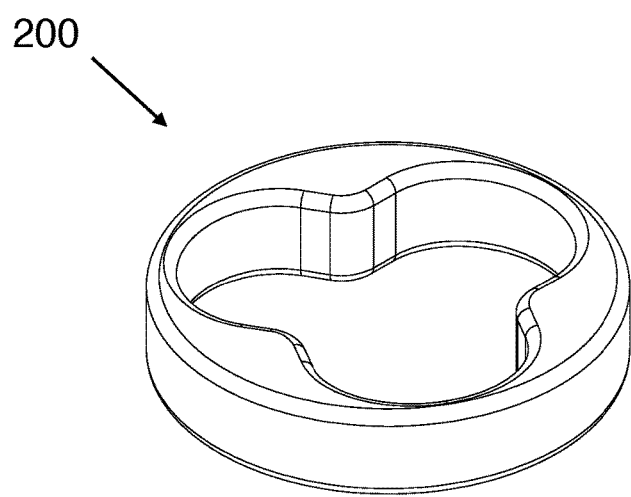
Figure 4C:
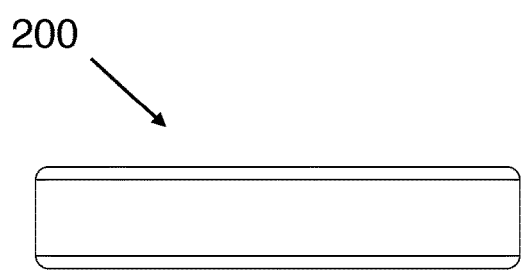

In the Summary above and in this Detailed Description, and the claims below, and in the accompanying drawings, reference is made to particular features of the invention. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any items, so a "set of items," may indicate the presence of only one item, or may indicate more items. Thus, the term "set" may be equivalent to "one or more" as used herein.

In the following detailed description, numerous specific details are set forth in order to provide a more thorough understanding of the one or more embodiments described herein. However, it will be apparent to one of ordinary skill in the art that the invention may be practiced without these specific details. In other instances, well-known features have not been described in detail to avoid unnecessarily complicating the description.

The present disclosure is generally drawn to a system and method, according to one or more exemplary embodiments, for a sizing device and erectile ring. The sizing device properly measures one's girth to correctly find the proper erection ring. The sizing device has a measuring tape that will slide through a plurality of perimeter components with a track running through the parts for the measuring tape to easily travel through. A measurement is then obtained when the perimeter components come into contact with an erected penis when an erection is created from the sizing.

With reference now to FIG. 1A-1D, one exemplary embodiment of sizing device 100 is shown. The main components of sizing device 100 include three perimeter components 110, tape measuring strip 120, and a holder 130. However, this is non-limiting and there may be any number of perimeter components in any arrangement. Sizing device 100 may be made of silicone or several different materials may be used depending on rigidity versus elasticity where sizing device 100 would have to be adjusted in size to maintain a proper fit.

Perimeter components 110 may have an overall hat shape directed inward with a rectangular arching outer portion and a bulbous inner portion designed to come into contact with the outer perimeter of the penis of a user. Perimeter components 110 may have an outer convex surface 115 on one end and two inner concave surfaces 116 on an opposite end. Inner concave surfaces 116 extend into an inner convex surface 117 positioned between inner concave surfaces 116 with a curve facing an opposite direction from the curve in outer convex surface 115. The length of outer convex surface 115 is equal to the length of inner concave surfaces 116 and inner convex surface 117. Inner convex surface 117 and inner concave surfaces 116 have deeper bends than outer convex surface 115. An aperture 118 that runs the length of perimeter components 110 with a first and second end may be positioned between inner concave surfaces 116 and outer convex surface 115.

Aperture 118 may be sized to provide access for a length of tape measure strip 120 to enter and exit perimeter components 110. Aperture 118 may have one or more tracks or guiding rails to assist in properly moving tape measure strip 120 through perimeter components 110. In one or more non-limiting embodiments, tape measure strip 120 comprises one or more measurement markings, scale, or demarcations such that a user can readily identify the circumference needed for an erectile ring.

A starting portion of tape measure strip 120 may be removably connected to a holder 130 at a first end. Holder 130 is attached to a perimeter component 110 at a second end. An end portion of the length of tape measure strip 120 may be positioned through perimeter component 110 and an aperture on holder 130 whereby the other end is protruding out of the aperture on one side of holder 130.

Holder 130 may have a series of gripping mechanisms or latch mechanisms whereby the user may adjust the circumference of the system to accommodate for varying distances between the penis and perimeter components 110. When engaged, the latch mechanisms allow tape measure strip 120 to move relative to perimeter components 110. When disengaged, the latch mechanism may prevent any further movement in the direction to increase the size of the circumference. Holder 130 may have an opening such that the user may read the measurement on tape measure strip 120.

Once measured, an erectile ring may be formed according to the specifications as determined and shipped or delivered to the user. One embodiment of an erectile ring is shown in FIGS. 2A-2C, FIGS. 3A-3B, and FIGS. 4A-4C. Erectile ring 200 may have a circular shape with an outer perimeter 220. Erectile ring 200 may have an inner three prong aperture with three concave surfaces 230 with the curve extending outward to the outer perimeter 220. Between each concave surface 230 may be a convex surface facing inward to a center of the aperture of erectile ring 200.

Figure 5A:
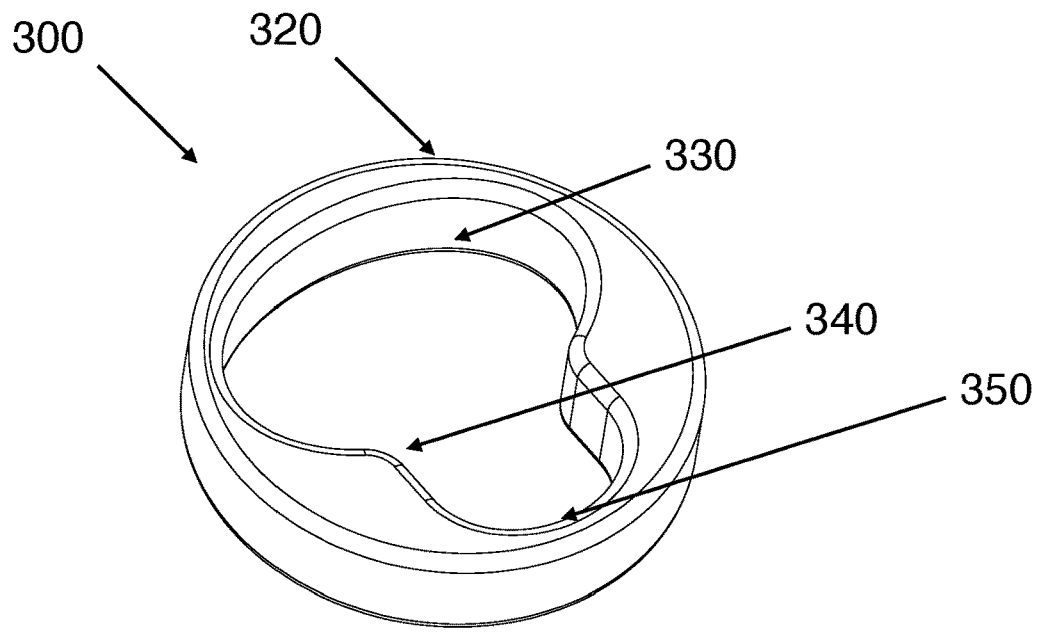
FIG. 5A-5C illustrates another embodiment of an erectile ring
Figure 5B:
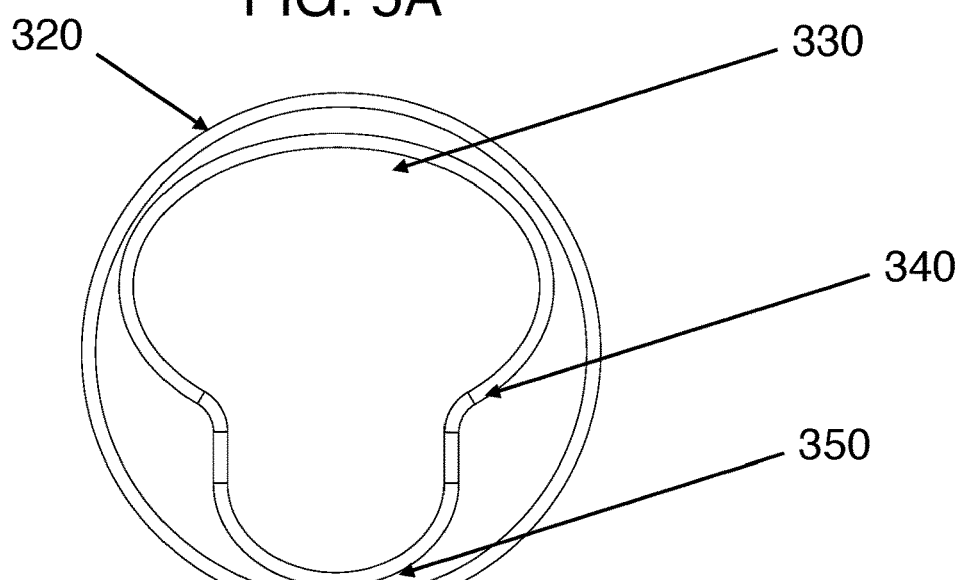
Figure 5C:
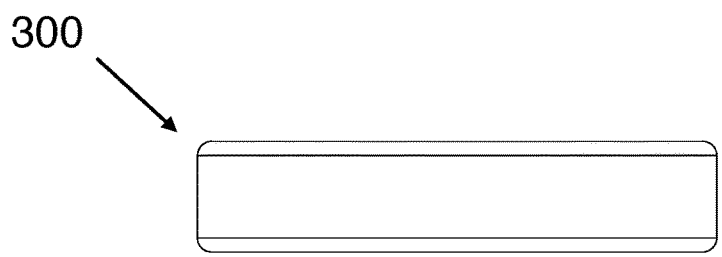

Another embodiment of an erectile ring is shown in FIG. 5A-5C. Erectile ring 300 may have a circular shape with an outer perimeter 320. Erectile ring 300 may have a mushroom shape inner aperture with a long arching concave surface 330 with the curve extending outward to the outer perimeter 320. Connected to concave surface 330 may be two convex surfaces 340 inward to a center of the aperture of erectile ring 300. Convex surfaces 340 extend into a concave surface 350 positioned between inner convex surfaces 340 with a curve facing an opposite direction from the curve in concave surface 330. Concave surface 330 may be longer than concave surface 350 while concave surface 350 may have a deeper bend.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the use contemplated.

What is claimed is:

1. A sizing device for a penis, the sizing device comprising: a plurality of components and a measurement strip, wherein each component of the plurality of components has a slot for providing access to a length of the measurement strip to pass through.

2. The sizing device of claim 1 further comprising: a holder connected to one component of the plurality of components wherein one end of the measurement strip is connected to the holder, wherein a second end of the measurement strip passes through the holder.

3. The sizing device of claim 2, wherein the holder has a latch mechanism for gripping the measurement strip.

4. The sizing device of claim 1, wherein each of the components of the plurality of components have a rectangular arching outer portion and a bulbous inner portion configured to come into contact with an outer perimeter of the penis.

5. The sizing device of claim 1, wherein each of the components of the plurality of components has an outer convex surface on one end and two inner concave surfaces on an opposite end, the inner concave surfaces extending into an inner convex surface positioned between the inner concave surfaces, the inner convex surface having a curve facing an opposite direction from a curve in the outer convex surface.

6. The sizing device of claim 5, wherein a length of the outer convex surface is equal to a length of the inner concave surfaces and the inner convex surface.

7. The sizing device of claim 6, wherein the inner convex surface and the inner concave surfaces have deeper bends than the outer convex surface.

8. A sizing system for a penis comprising: a sizing device and an erectile ring, the sizing device having a plurality of components and a measurement strip, each component of the plurality of components having a slot for providing access to a length of the measurement strip to pass through.

9. The sizing system of claim 8, wherein the sizing device has a holder connected to one of the plurality of components wherein one end of the measurement strip is connected to the holder, wherein a second end of the measurement strip passes through the holder.

10. The sizing system of claim 9, wherein the holder has a latch mechanism for gripping the measurement strip.

11. The sizing system of claim 8, wherein each component of the plurality of components has a rectangular arching outer portion and a bulbous inner portion configured to come into contact with an outer perimeter of the penis.

12. The sizing system of claim 8, wherein each component of the plurality of components has an outer convex surface on one end and two inner concave surfaces on an opposite end, the two inner concave surfaces extending into an inner convex surface positioned between the two inner concave surfaces, the inner convex surface having a curve facing an opposite direction from a curve in the outer convex surface.

13. The sizing system of claim 12, wherein a length of the outer convex surface is equal to the length of the two inner concave surfaces and the inner convex surface.

14. The sizing system of claim 13: the inner convex surface and the inner concave surfaces have deeper bends than the outer convex surface.

15. The sizing system of claim 8, wherein the erectile ring is circular with an aperture having three inner three prongs.

16. The sizing system of claim 8, wherein the sizing system has an aperture with three concave surfaces with a curve extending outward to an outer perimeter, wherein between each concave surface there is convex surface facing inward to a center of the aperture.

17. The sizing system of claim 8, wherein the sizing system has an aperture with an arching concave surface with a curve extending outward to an outer perimeter, wherein the arching concave surface is connected to two convex surfaces inward to a center of the aperture, the two convex surfaces extending into a second concave surface positioned between the two convex surfaces.

18. A method for a sizing device for a penis, the method including: measuring the penis with a sizing device comprising: a plurality of components and a measurement strip, each component of the plurality of components having a slot for providing access to a length of the measurement strip to pass through, the sizing device having a holder connected to one component of the plurality of components wherein one end of the measurement strip is connected to the holder, wherein a second end of the measurement strip passes through the holder.

19. The method of claim 18 further comprising: creating an erectile ring in response to the measurement, wherein the erectile ring has an aperture with three concave surfaces with a curve extending outward to an outer perimeter, wherein between each concave surface there is convex surface facing inward to a center of the aperture.

20. The method of claim 18 further comprising: creating an erectile ring in response to the measurement, wherein the erectile ring has an aperture with an arching concave surface with a curve extending outward to an outer perimeter, wherein the arching concave surface is connected to two convex surfaces inward to a center of the aperture, the two convex surfaces extending into a second concave surface positioned between the two convex surfaces.

* * * * *